(12) United States Patent
Nguyen

(10) Patent No.: US 10,362,969 B2
(45) Date of Patent: Jul. 30, 2019

(54) IMAGE-BASED DETECTION AND DIAGNOSIS OF DIASTASIS RECTI

(71) Applicant: Sensors Unlimited, Inc., Princeton, NJ (US)

(72) Inventor: Thuc-Uyen Nguyen, Princeton, NJ (US)

(73) Assignee: Sensors Unlimited, Inc., Princeton, NJ (US)

(*) Notice: Subject to any disclaimer, the term of this patent is extended or adjusted under 35 U.S.C. 154(b) by 460 days.

(21) Appl. No.: 15/146,636

(22) Filed: May 4, 2016

(65) Prior Publication Data

US 2017/0319107 A1   Nov. 9, 2017

(51) Int. Cl.
| | |
|---|---|
| A61B 5/00 | (2006.01) |
| A61B 5/103 | (2006.01) |
| H04N 5/33 | (2006.01) |
| A61B 5/107 | (2006.01) |
| G01N 21/359 | (2014.01) |
| G01N 21/3563 | (2014.01) |
| G06T 7/73 | (2017.01) |

(52) U.S. Cl.
CPC ............ *A61B 5/1072* (2013.01); *A61B 5/002* (2013.01); *A61B 5/0022* (2013.01); *A61B 5/0077* (2013.01); *A61B 5/4519* (2013.01); *A61B 5/7282* (2013.01); *A61B 5/742* (2013.01); *A61B 5/0086* (2013.01); *A61B 5/103* (2013.01); *A61B 5/107* (2013.01); *A61B 5/4538* (2013.01); *G01N 21/359* (2013.01); *G01N 21/3563* (2013.01); *G06T 7/74* (2017.01); *G06T 2207/10048* (2013.01); *H04N 5/332* (2013.01)

(58) Field of Classification Search
CPC ....... A61B 5/103; A61B 5/107; A61B 5/1072; A61B 5/4519; A61B 5/4538; A61B 5/002; A61B 5/0022; A61B 5/0077; A61B 5/0086; A61B 5/7282; A61B 5/742; G06T 2207/10048; G01N 21/3563; G01N 21/359; H04N 5/332
See application file for complete search history.

(56) References Cited

U.S. PATENT DOCUMENTS

| | | | |
|---|---|---|---|
| 7,149,567 B2 | 12/2006 | Demos et al. | |
| 8,792,968 B2 | 7/2014 | Xiao et al. | |
| 2011/0149094 A1* | 6/2011 | Chen | H04N 5/23248 348/208.3 |

OTHER PUBLICATIONS

Lih-Jiun Liaw, Miao-Ju Hsu, Chien-Fen Liao, Mei-Fang Liu, Ar-Tyan Hsu; the Relationships Between Inter-recti Distance Measured by Ultrasound Imaging and Abdominal Muscle Function in Postpartum Women: A 6-Month Follow-up Study; published on Jun. 2011; Journal of Orthopaedic & Sports Physical Therapy, 2011 vol. 41 Issue:6 pp. 435-443.*

(Continued)

*Primary Examiner* — Amanda Lauritzen Moher
*Assistant Examiner* — Chao Sheng
(74) *Attorney, Agent, or Firm* — Locke Lord LLP; Scott D. Wofsy; Joshua L. Jones

(57) ABSTRACT

A method for diagnosing a condition of a subject includes imaging an abdominal area of the subject to obtain one or more images of the abdominal area. Separation between rectus abdominis muscles in the abdominal area is located from the one or more images. Distance of the separation between the rectus abdominis muscles is quantified. The results of the quantified distance and one or more images are outputted on one or more display units.

17 Claims, 3 Drawing Sheets

(56) References Cited

OTHER PUBLICATIONS

Mohammed Kamruzzaman, Gamal ElMasry, Da-Wen Sun, Paul Allen; Application of NIR hyperspectral imaging for discrimination of lamb muscles; published online on Dec. 30, 2010; Journal of Food Engineering 104 (2011); pp. 332-340.*

Yvonne Coldron, Maria J. Stokes, Di J. Newham, Katy Cook; Postpartum characteristics of rectus abdominis on ultrasound imaging; published on Apr. 2008; Manual Therapy; vol. 13, Issue 2, pp. 112-121.*

\* cited by examiner

IMAGE-BASED DETECTION AND DIAGNOSIS OF DIASTASIS RECTI

FIELD

Embodiments herein relate to imaging, and more particularly to imaging such as used in image-based detection and diagnosis of diastasis recti.

BACKGROUND

Diastasis recti is a condition in which the connective tissue connecting the two sides of the rectus abdominis muscle is stretched. This condition is most often found in newborns, pregnant women, and people with incorrect exercise routines. Diastasis recti can lead to hernia, pain, cosmetic issues, and can worsen with unsuitable postures and workout routines. If left untreated, diastasis recti can result in various medical problems, some of which could be disabling, including hernias, lower back pain and other complications. Common detection methods currently used include visual observation with rough measurement of the muscle gap or ultrasound. For example, the prevalent method is for a medical professional to place as many fingers into the muscle gap as will fit. If two or more fingertips fit within the gap, the medical professional might infer presence of diastasis recti. However, this method can lead to variations in diagnosis due to variation from one medical professional to another in finger size and/or technique.

Conventional methods and systems have generally been considered satisfactory for their intended purpose. However, there is still a need in the art for systems and methods that provide for improved detection and diagnosis of diastasis recti. The present disclosure provides a solution for this need.

SUMMARY

A method for diagnosing a condition of a subject includes imaging an abdominal area of the subject to obtain one or more images of the abdominal area. Separation between rectus abdominis muscles in the abdominal area is identified in the one or more images. Distance across the separation between the rectus abdominis muscles is quantified from the one or more images. The results of the quantified distance and one or more images are outputted, e.g., as a printout, on one or more display units, or by other suitable means of outputting.

Imaging the abdominal area can include using an imaging sensor sensitive to near-infrared radiation and/or shortwave infrared radiation. It is also contemplated that imaging can include illuminating the abdominal area with a shortwave infrared (SWIR) and/or near-infrared (NIR) illumination source.

Identifying the separation can include characterizing one or more regions in the one or more images based on value. Low value regions can be indicative of regions containing fluid and high value regions can be indicative of regions containing muscle. The separation can define a low value region in the one or more images. The method can further include using automated edge detection to identify one or more regions in the abdominal area.

Quantifying the distance can include measuring a span of the low value region. Quantifying the distance can include correcting the one or more images for camera pose so that the distance is true distance measured relative to the subject in the one or more images.

The method can further include making a determination of whether a diastasis recti condition is present based on the quantified distance. The diastasis recti condition can be diagnosed when the quantified distance exceeds a threshold. Making a determination of whether the diastasis recti condition is present can include utilizing abdominal imaging data from a database.

A system for diagnosing a condition of a subject includes one or more imaging components, and a processor operatively coupled to a memory having instructions stored thereon that, when executed by the processor, causes the processor to perform an embodiment of the method described above or described herein.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures.

DETAILED DESCRIPTION

Figure 1:
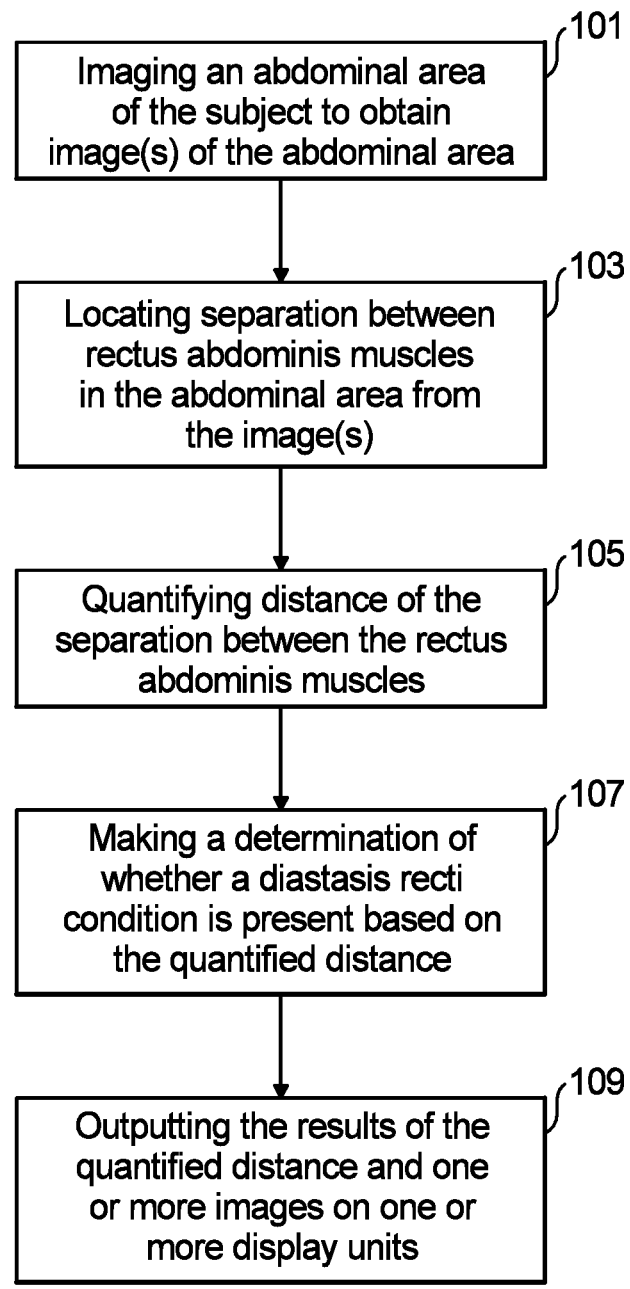
FIG. 1 is a schematic view of an exemplary embodiment of a method for diagnosing a condition (e.g., diastasis recti) in accordance with the present disclosure.

Reference will now be made to the drawings wherein like reference numerals identify similar structural features or aspects of the subject disclosure. For purposes of explanation and illustration, and not limitation, a partial view of an exemplary embodiment of a method and system for image-based detection and diagnosis of a medical condition in accordance with the disclosure is shown in FIG. 1 and is designated generally by reference character 100. Other embodiments of the system and method in accordance with the disclosure, or aspects thereof, are provided in FIGS. 2 and 3, as will be described. Systems and methods described herein can be used for diagnosing and detecting a condition in a subject, for example, a medical condition such as diastasis recti.

Diastasis recti is a condition in which separation between the right and left rectus abdominis muscles occurs. Commonly, the separation or gap may be 2.7 centimeters (cm) or greater between the two sides of the rectus abdominis muscle. While this condition has no associated morbidity or mortality, if left untreated, diastasis recti can result in various medical problems.

Current methods of diagnosing diastasis recti include a physician feeling the tenderness of the muscles under the abdominal area to see if the area is soft or hard and using his/her fingers to assess the size of any detected gaps in the abdominal area. For example, a physician may diagnose diastasis recti based on the number of fingers that can fit in between the separated muscles. This method can be highly inaccurate and subjective. Another method of diagnosis includes the use of ultrasound. However, performing ultrasounds can be cost prohibitive.

Embodiments herein provide early detection of diastasis recti, identify potential risks associated therewith, help patients adjust their activities and lifestyles to minimize further muscle separation, and aid in surgery decision. Compared to traditional techniques, the diagnosis is less subjective, and more easily incorporated with digital medical records, especially if combined with digital image processing to quantify the level of muscle separation. Diagnosis and detection are unaffected by other imaging features, such as skin color.

Referring to the figures, FIG. 1 shows an illustrative method 100 for diagnosing diastasis recti according to an embodiment herein. An abdominal area of a subject can be imaged 101 using one or more imaging devices to obtain image(s) of the abdominal area. For example, the one or more imaging devices may include a near-infrared (NIR) sensitive and/or a shortwave infrared (SWIR) sensitive device (e.g., a sensor or camera). The one or more images may be digitized and stored, for example, in a database such as database 330 of FIG. 3.

The separation between the rectus abdominis muscles in the abdominal area can be located 103 from the image(s). The muscle separation is revealed with high contrast when an infrared camera is used for imaging the abdominal area. The area of muscle separation typically has higher absorption due to the lack of light blocking muscles, thereby revealing the more absorptive fluids and organs underneath (e.g., blood, water, etc.). As such, in an image of the abdominal area captured by an infrared camera, the muscles/tissue mass would be represented by higher value regions. On the other hand, the areas with lower value would be indicative of regions with an increased volume of blood/water, which in the abdominal region corresponds to a gap between muscles/tissues. As used herein, value may refer to brightness or darkness in the image.

The distance of the separation between the rectus abdominis muscles can be quantified 105. Calculation of the distance of the separation can be performed by an algorithm to measure/quantify muscle separation and distance/size of the gap. For example, the various regions in the one or more images can be categorized into regions having muscles or regions having fluid based on contrast/value. Categorization can be performed using edge detection and/or image processing and segmentation techniques. Regions of lower value corresponding to areas of separation can be measured, for example, the span/size of the low value region can be measured and quantified. Size reference can be obtained from a database for comparison, which helps for clinical repeatability. Quantifying the distance can include correcting the one or more images for camera pose so that the distance is true distance measured relative to the subject in the one or more images.

A determination of whether a diastasis recti condition is present can be made 107 based on the quantified distance. For example, the determination can be made based on a comparison between the quantified distance and data from a database (e.g., database 330 of FIG. 3) and/or if the quantified distance exceeds a threshold (e.g., greater than or equal to 2.7 cm). The threshold can be pre-set or determined by a user or physician. The results of the quantified distance and one or more images can be outputted 109, for example, on one or more display units such as a screen of a computing device, as a printout, or any other suitable means of output. The results can be viewed and evaluated by a user, a physician, etc. The results can also be stored in a database such as database 330 described in the context of FIG. 3 below.

Figure 2:
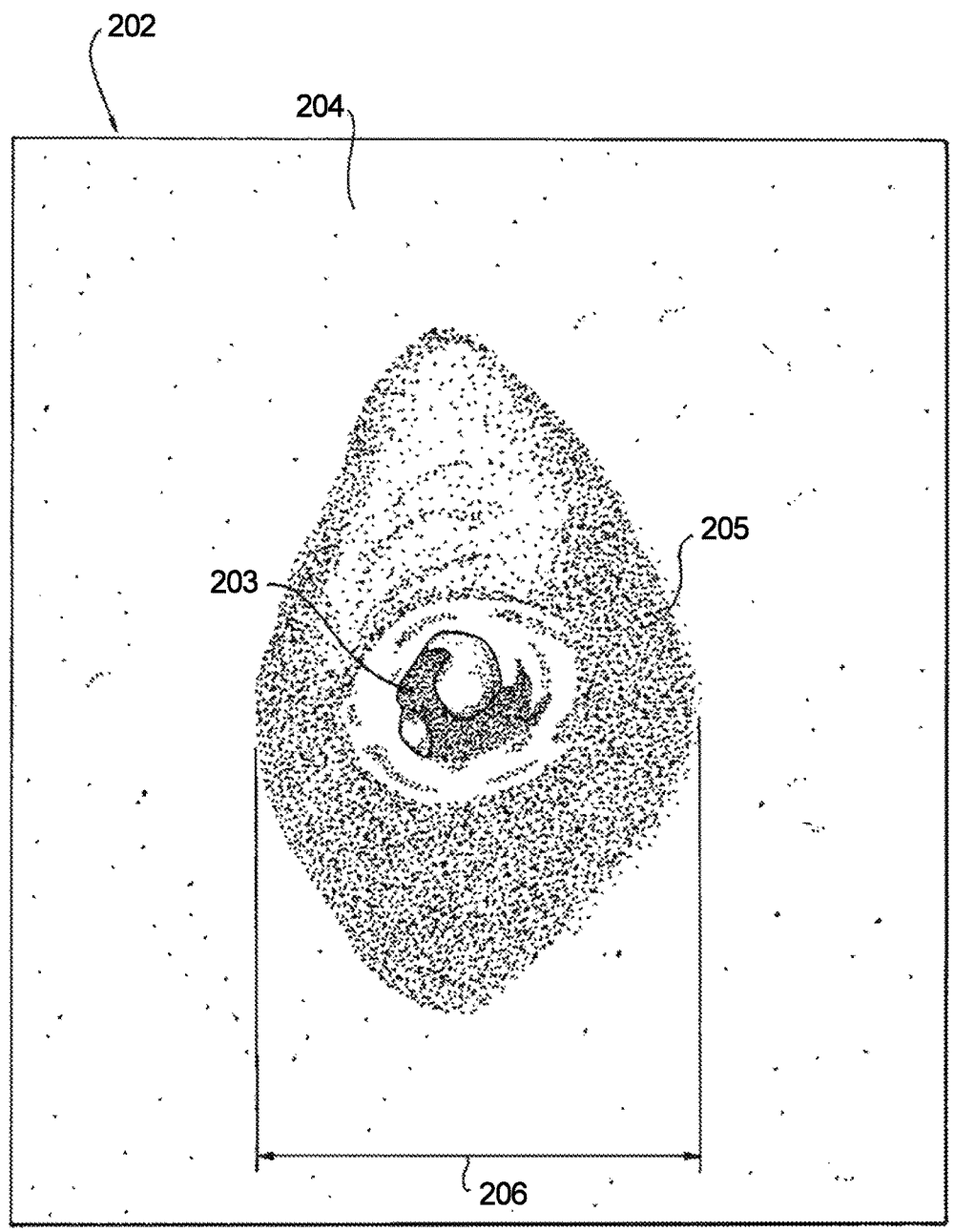
FIG. 2 is an exemplary image of an abdominal area obtained using a system implementing the method of FIG. 1.

FIG. 2 shows an illustrative image 202 of an abdominal area of a subject obtained using a system implementing the method described in the context of FIG. 1 above. As shown, image 202 includes a navel 203 and regions surrounding the navel 203. Image 202 includes a high value region 203, which is indicative of regions of the abdomen having muscles/tissue mass. Image 202 can also include a low value region 205, which is indicative of a region of the abdomen having fluid underneath. A quantified distance 206 of the separation between the right and left rectus abdominis muscles can be calculated and indicated on image 202. The calculation can be performed according to method 100 described above.

Figure 3:
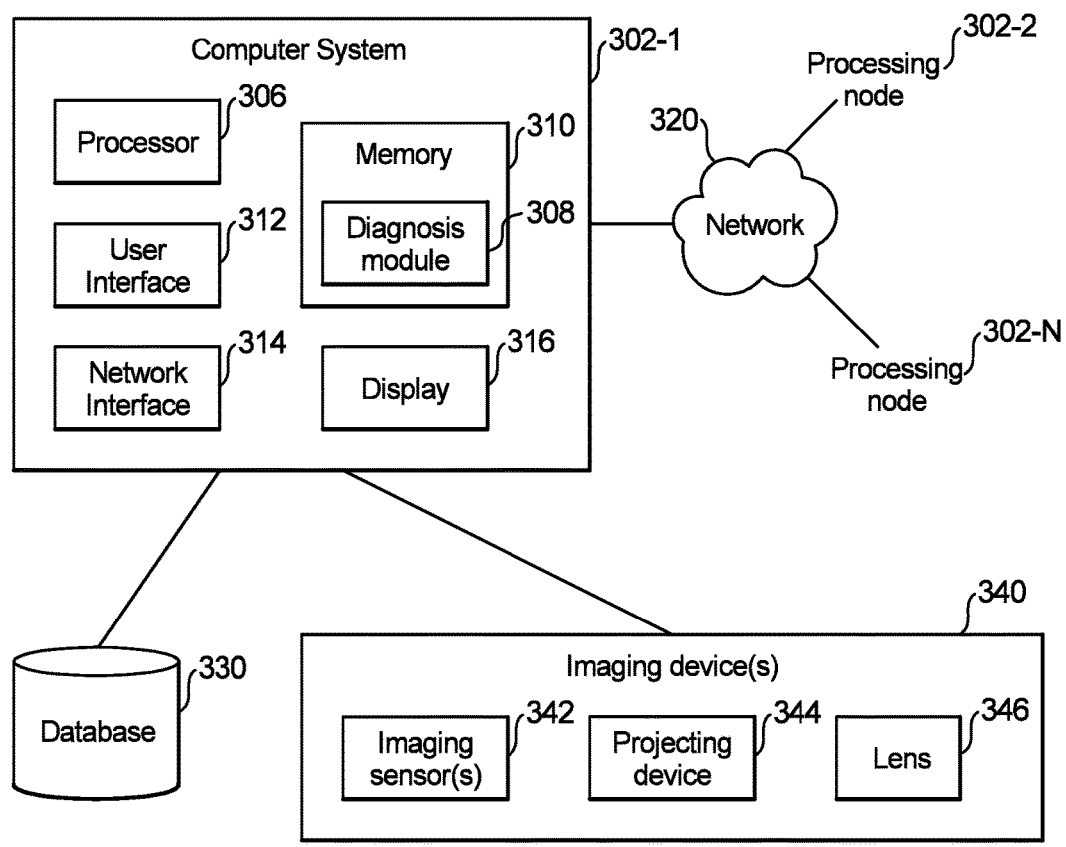
FIG. 3 is a schematic view of an exemplary system for implementing an embodiment of the method shown in FIG. 1.

FIG. 3 depicts a system 300 for implementing methodology 100 of FIG. 1. System 300 includes processing nodes 302-1 . . . 302-N, configured to communicate over a network 320. Each of processing nodes 302-1 . . . 302-N may be configured as shown in computer system 302-1, which may include, but is not limited to, personal computer systems, server computer systems, hand-held or laptop devices, multiprocessor systems, microprocessor-based systems, programmable consumer electronics, network PCs, and the like. Computer system 302-1 may include one or more processors 306 coupled to a memory 310, a user interface 312, a network interface 314 and a display 316. Memory 310 may include instructions stored thereon, that when executed by processor 306, causes the processor 306 to perform any embodiments of method 100. Memory 310 may comprise a diagnosis module 308 for implementing one or more steps of methodology 100 of FIG. 1.

System 300 may also include a database 330 configured to communicate with processing nodes 302-1 . . . 302-N. The database 330 may include information for diagnosing medical conditions such as diastasis recti. For example, database 330 may include data and/or images on previously recorded quantified distance of the separation between the left and right rectus abdominis muscles. The diagnosis module 308 can be configured to execute machine readable instructions to identify medical conditions such as diastasis recti utilizing data from the database 330.

System 300 may also include one or more imaging devices 340. The imaging device(s) 340 may contain one or more imaging sensors 342 and lens 346 and may contain a source of illumination or projecting device 344. Imaging sensors 342 may be sensitive to any portion of the electromagnetic spectrum, but can advantageously include one imaging sensor sensitive to the visible spectrum and one sensor sensitive to the near-infrared spectrum. Projecting device 344 optionally provides illumination, and/or projects fiducial marks, and/or projects imagery useful in pose and range estimation, in a segment of the electromagnetic spectrum that may overlap, at least in part, the sensitive spectrum of imaging device 340. The illumination provided by projecting device 344 may be automatically adapted by diagnosis module 308 or may be controlled by a user through user interface 312. Similarly, any polarization of radiation from projecting device 344 and polarization of radiation received by sensors 342 may be automatically adapted by diagnosis module 308 or may be controlled by a user through user interface 312. The automatic adaptation may be achieved by automatically varying the illumination and/or polarization to optimize one or more image quality metrics.

User interface 312 may be configured to enable user input into the computer system 302-1. Display 316 may be configured to display results of method 100. Network interface 314 may be configured to enable the computer system 302-1 to interface with a network 320 and other system components. Network 320 may be a communication link comprising an internet connection, Ethernet link, local area link, cellular link, satellite link, global system for mobile communication (GSM), etc. It is to be appreciated that system 300 may include more or less components than shown in FIG. 3.

As will be appreciated by those skilled in the art, aspects of the present disclosure may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "device," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1 is intended to provide a brief, general description of an illustrative and/or suitable exemplary method according to which embodiments of the above described present invention may be implemented. FIG. 1 is exemplary of a suitable method and is not intended to suggest any limitation as to the structure, scope of use, or functionality of an embodiment of the present invention. A particular method should not be interpreted as having any dependency or requirement relating to any one or combination of components illustrated in an exemplary operating method. For example, in certain instances, one or more elements of the method may be deemed not necessary and omitted. In other instances, one or more other elements may be deemed necessary and added.

The methods and systems of the present disclosure, as described above and shown in the drawings, provide for detection and diagnosis of a medical condition such as diastasis recti. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for diagnosing a condition of a subject, comprising:
   imaging surface skin of an abdominal area in vivo, using an imaging sensor sensitive to infrared radiation, of the subject to obtain one or more images of the abdominal area;
   identifying subcutaneous features including separation between rectus abdominis muscles in the abdominal area in the one or more images;
   quantifying distance across the separation between the rectus abdominis muscles from the one or more images; and
   outputting the results of the quantified distance and one or more images.

2. The method of claim 1, wherein the imaging sensor is sensitive to near-infrared radiation.

3. The method of claim 1, wherein the imaging sensor is sensitive to short-wavelength infrared radiation.

4. The method of claim 1, wherein imaging the abdominal area includes illuminating the abdominal area with at least one of a near-infrared illumination source and a shortwave infrared illumination source.

5. The method of claim 1, further comprising using automated edge detection to identify one or more regions in the abdominal area.

6. The method of claim 1, wherein identifying the separation includes characterizing one or more regions in the one or more images based on value.

7. The method of claim 6, wherein low value regions are indicative of regions containing fluid and high value regions are indicative of regions containing muscle.

8. The method of claim 7, wherein the separation defines a low value region in the one or more images.

9. The method of claim 8, wherein quantifying the distance includes measuring a span of the low value region.

10. The method of claim 9, further comprising making a determination of whether a diastasis recti condition is present based on the quantified distance.

11. The method of claim 10, further comprising diagnosing the diastasis recti condition when the quantified distance exceeds a threshold.

12. A system for diagnosing a condition of a subject, comprising:
   one or more imaging components; and
   a processor operatively coupled to a memory having instructions stored thereon that, when executed by the processor, causes the processor to:
      image surface skin of an abdominal area in vivo, using an imaging sensor sensitive to infrared radiation, of the subject to obtain one or more images of the abdominal area;
      identify subcutaneous features including separation between rectus abdominis muscles in the abdominal area in the one or more images;
      quantify distance across the separation between the rectus abdominis muscles from the one or more images; and
      output the results of the quantified distance and one or more images.

13. The system of claim 12, wherein the image sensor is sensitive to near-infrared radiation.

14. The system of claim 12, wherein the image sensor is sensitive to shortwave infrared radiation.

15. The system of claim 12, further comprising at least one of a near-infrared illumination source and a shortwave infrared illumination source for imaging the abdominal area.

16. The system of claim 12, wherein quantifying the distance includes measuring a span of low value region defined as the separation between the rectus abdominis muscles.

17. The system of claim 12, wherein the processor is further configured to make a determination of whether a diastasis recti condition is present based on the quantified distance.

* * * * *